United States Patent
Swazey et al.

(10) Patent No.: US 9,045,716 B2
(45) Date of Patent: *Jun. 2, 2015

(54) SURFACTANT THICKENED SYSTEMS COMPRISING MICROFIBROUS CELLULOSE AND METHODS OF MAKING SAME

(75) Inventors: John M. Swazey, San Diego, CA (US); Neil A. Morrison, San Diego, CA (US)

(73) Assignee: CP Kelco U.S., Inc., Atlanta, GA (US)

( * ) Notice: Subject to any disclaimer, the term of this patent is extended or adjusted under 35 U.S.C. 154(b) by 1065 days.

This patent is subject to a terminal disclaimer.

(21) Appl. No.: 11/557,622

(22) Filed: Nov. 8, 2006

(65) Prior Publication Data

US 2008/0108714 A1 May 8, 2008

(51) Int. Cl.
| | |
|---|---|
| C11D 17/04 | (2006.01) |
| B01F 17/00 | (2006.01) |
| C11D 3/22 | (2006.01) |
| A61K 8/02 | (2006.01) |
| A61K 8/04 | (2006.01) |
| A61K 8/73 | (2006.01) |
| A61Q 19/10 | (2006.01) |
| C11D 17/00 | (2006.01) |
| B01F 3/12 | (2006.01) |

(52) U.S. Cl.
CPC . *C11D 3/22* (2013.01); *A61K 8/027* (2013.01); *A61K 8/044* (2013.01); *A61K 8/731* (2013.01); *A61Q 19/10* (2013.01); *C11D 17/003* (2013.01)

(58) Field of Classification Search
CPC ...... C11D 17/003; C11D 3/222; A61K 8/027; A61K 8/044; A61K 8/731; A61Q 19/10
USPC ........................ 516/31, 77, 106; 510/416, 418; 106/162.8
See application file for complete search history.

(56) References Cited

U.S. PATENT DOCUMENTS

| | | | |
|---|---|---|---|
| 3,858,854 A | | 1/1975 | Win et al. |
| 3,975,536 A | * | 8/1976 | Stevenson et al. ............ 514/456 |
| 4,378,381 A | * | 3/1983 | Turbak et al. ................. 426/570 |
| 4,379,059 A | | 4/1983 | Hockey et al. |
| 4,452,722 A | * | 6/1984 | Turbak et al. ................. 516/106 |
| 4,483,743 A | * | 11/1984 | Turbak et al. ................. 162/100 |
| 4,500,546 A | * | 2/1985 | Turbak et al. ................. 514/781 |
| 5,087,471 A | * | 2/1992 | Combes et al. ................ 426/573 |
| 5,441,753 A | * | 8/1995 | McGinley et al. ............. 426/96 |
| 5,951,910 A | | 9/1999 | Skaggs |
| 5,998,349 A | | 12/1999 | Guillou |
| 6,224,663 B1 | * | 5/2001 | Cantiani et al. ............ 106/162.8 |
| 6,231,651 B1 | | 5/2001 | Schultz et al. |
| 6,241,812 B1 | * | 6/2001 | Smith et al. ................. 106/162.8 |
| 6,302,209 B1 | | 10/2001 | Thompson et al. |
| 6,306,207 B2 | | 10/2001 | Cantiani et al. |
| 6,846,785 B2 | | 1/2005 | Patel et al. |
| 6,967,027 B1 | * | 11/2005 | Heux et al. ................... 424/488 |
| 7,776,807 B2 | * | 8/2010 | Canto et al. .................. 510/151 |
| 7,888,308 B2 | * | 2/2011 | Swazey ......................... 510/470 |
| 7,981,855 B1 | * | 7/2011 | Palla-Venkata et al. ...... 510/462 |
| 7,994,111 B2 | * | 8/2011 | Caggioni et al. .............. 510/473 |
| 8,097,574 B2 | * | 1/2012 | Heath et al. .................... 510/137 |
| 8,361,239 B2 | * | 1/2013 | Bettiol et al. ................. 134/25.2 |
| 8,470,755 B1 | * | 6/2013 | Tajmamet et al. ............ 510/237 |
| 8,541,355 B2 | * | 9/2013 | Fleckenstein et al. ........ 510/405 |
| 8,546,318 B2 | * | 10/2013 | D'Ambrogio et al. ........ 510/470 |
| 8,642,529 B2 | * | 2/2014 | Palla-Venkata et al. ...... 510/471 |
| 2003/0109391 A1 | | 6/2003 | Midha et al. |
| 2003/0162689 A1 | | 8/2003 | Schymitzele |
| 2004/0267006 A1 | | 12/2004 | Yamane |
| 2005/0119151 A1 | | 6/2005 | Mayer et al. |
| 2006/0029625 A1 | | 2/2006 | Niebauer |
| 2006/0083761 A1 | | 4/2006 | Yoshimi et al. |
| 2006/0110416 A1 | * | 5/2006 | Ryles et al. ................... 424/401 |
| 2006/0127345 A1 | | 6/2006 | Hilvert et al. |
| 2006/0281859 A1 | | 12/2006 | Suzuki et al. |
| 2007/0027108 A1 | * | 2/2007 | Yang et al. ...................... 514/57 |
| 2007/0197779 A1 | | 8/2007 | Yang et al. |
| 2008/0108541 A1 | * | 5/2008 | Swazey ......................... 510/535 |
| 2008/0108714 A1 | * | 5/2008 | Swazey et al. .................. 516/31 |
| 2009/0306254 A1 | * | 12/2009 | van der Wielen et al. ...... 524/44 |
| 2010/0009891 A1 | * | 1/2010 | Canto et al. ................... 510/418 |
| 2010/0016575 A1 | * | 1/2010 | Yang et al. ..................... 536/56 |
| 2011/0039744 A1 | * | 2/2011 | Heath et al. .................... 510/121 |
| 2011/0059883 A1 | * | 3/2011 | Swazey et al. ................. 510/320 |
| 2011/0104096 A1 | * | 5/2011 | Swazey ....................... 424/70.13 |
| 2012/0122998 A1 | * | 5/2012 | Palla-Venkata et al. ...... 514/781 |
| 2012/0309662 A1 | * | 12/2012 | D'Ambrogio et al. ........ 510/218 |
| 2013/0274149 A1 | * | 10/2013 | Lafitte et al. .................. 507/112 |
| 2014/0128480 A1 | * | 5/2014 | Swazey et al. ................ 514/781 |

FOREIGN PATENT DOCUMENTS

| | | |
|---|---|---|
| EP | 0859011 A | 8/1998 |
| GB | 2379223 A * | 8/2001 |

(Continued)

OTHER PUBLICATIONS

Ash, Michael Ash, Irene (2005; 2008). Handbook of Industrial Surfactants (4th Edition), pp. 1596 & 5487, Synapse Information Resources, Inc.. Online version available at: http://app.knovel.com/hotlink/toc/id:kpHISE000G/handbook-industrial-surfactants, (downloaded Oct. 17, 2013).*

(Continued)

*Primary Examiner* — Daniel S Metzmaier

(74) *Attorney, Agent, or Firm* — Sutherland Asbill & Brennan LLP

(57) ABSTRACT

Surfactant systems are provided using microfibrous cellulose to suspend particulates. In one embodiment the surfactant system includes a microfibrous cellulose at a concentration from about 0.05% to about 1.0% (w/w), a surfactant at a concentration of about 5% to about 50% (w/w active surfactant), and a particulate. Also provided herein are methods for preparing surfactant systems including microfibrous cellulose.

24 Claims, 4 Drawing Sheets

(56) References Cited

FOREIGN PATENT DOCUMENTS

| | | | |
|---|---|---|---|
| JP | 62172099 A | 7/1987 | |
| JP | 6043600 A | 6/1994 | |
| JP | 2000026229 A | 1/2000 | |
| JP | 2003095904 A | 4/2003 | |
| WO | 9940153 A1 | 8/1999 | |
| WO | 0047628 A2 | 8/2000 | |
| WO | WO 0105838 A1 * | 1/2001 | |
| WO | 0218486 | 3/2002 | |
| WO | 03062361 A1 | 7/2003 | |
| WO | 03085074 A1 | 10/2003 | |
| WO | WO 2004/074420 A1 * | 9/2004 | |
| WO | 2005048986 A1 | 6/2005 | |

OTHER PUBLICATIONS

Gangolli, S. (2005). Dictionary of Substances and Their Effects (Dose, 3rd Electronic Edition). Royal Society of Chemistry, p. C381. Online version available at: http://app.knovel.com/hotlink/toc/id:kpDSTEDOS3/dictionary-substances (downloaded Oct. 17, 2013).*

Jeen International Corp., JEETERIC CAB-LC Coco-amido-N-propyl-Betaine, Technical data sheet, (revision date Mar. 1, 2001), p. 1 of 1, online @ http://www.jeen.com/technical/SPEC%20JEETERIC%20CAB-LC.pdf (downloaded Oct. 17, 2013).*

Milton J. Rosen, Surfactants and Interfacial Phenomena, Third Edition, (Published Online: Aug. 31, 2004) John Wiley & Sons Inc, Hoboken, NJ, USA, pp. 105-106, 120-121, 127-130, 138-139.*

PCT Search report for PCT/US07/83422 mailed Mar. 19, 2008.

PCT Search report for PCT/US07/87229 mailed Apr. 9, 2008.

Australian Examination Report of Singapore 200903483-6, mailed Jan. 25, 2011, Australian Patent Office, pp. 1-7.

European Search Report/Opinion of EP07865575, mailed Dec. 1, 2011, EPO, The Hague, pp. 1-9.

Extended European Search Report/Opinion of EP07863824.4, mailed Mar. 9, 2011, EPO, The Hague, pp. 1-13.

Chinese Office Action Application No. 200780041617.6 Issued Dec. 21, 2010.

* cited by examiner

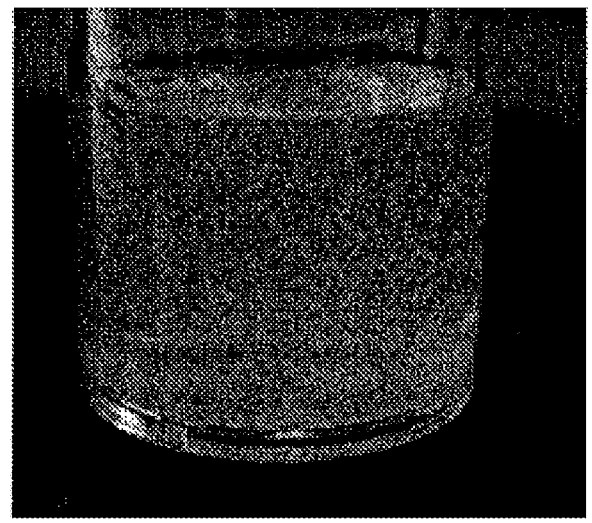
FIG. 1

FIG.2
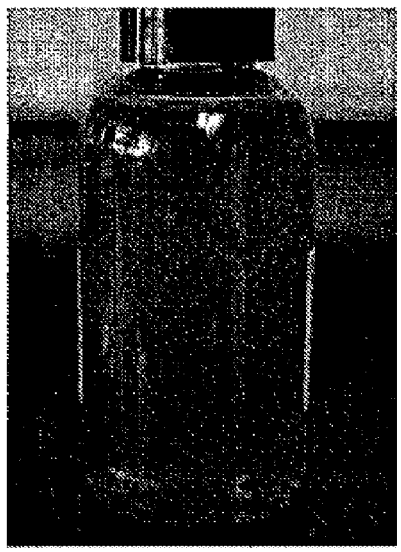
Palmolive Ultra Dish Soap
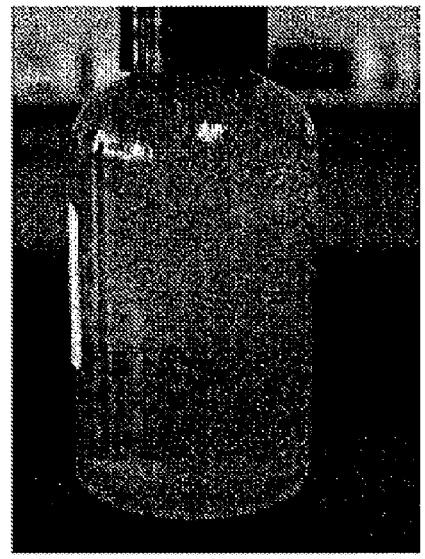
Dawn Ultra Dish Soap
FIG. 3

SURFACTANT THICKENED SYSTEMS COMPRISING MICROFIBROUS CELLULOSE AND METHODS OF MAKING SAME

BACKGROUND OF THE INVENTION

Surfactant-based products such as body washes, shampoos, dishwashing detergents, laundry detergents, and automotive detergents, among others, are often thickened by utilizing high concentration of surfactants, by combining viscosity synergistic surfactants, or by combining the surfactants with small amounts of salts, such as sodium salts. These formulations result in high viscosity products that appear rich and smooth but they are limited in that they do not provide sufficient low shear viscosity to allow for suspension of particles. Such particulates might include aesthetic agents (decorative beads, pearlescents, air bubbles, fragrance beads, etc.) or active ingredients (insoluble enzymes, encapsulated actives such as moisturizers, zeolites, exfoliating agents (e.g. alpha hydroxyl and/or glycolic acids or polyethylene beads), vitamins (e.g. vitamin E)) etc. or both.

Conventional thickeners and suspension aids such as xanthan gum, carboxymethyl cellulose (CMC), hydroxyethylcellulose (HEC), hydroxypropylmethylcellulose (HPMC), and many types of polyacrylates do not function well in surfactant-thickened systems and often lead to a loss of transparency due to clouding, gelling, and/or phase separation or lack sufficient suspension properties. For example, xanthan gum imparts excellent suspension properties in certain body wash formulations with low surfactant-thickening but the gum often loses its suspension ability in systems with high surfactant thickening, usually resulting in a hazy, irregular appearance, and a grainy or lumpy texture. Cellulosic products (CMC, HEC, HPMC, etc.), as another example of conventional thickeners, provide unreliable suspension and have significant limitations with respect to surfactant compatibilities. Acrylates systems are common, however, these systems do not always achieve a sufficient clarity level, require high concentrations of polymer, and are not considered natural. Salts are often capable of increasing high shear viscosity in surfactant-thickened systems but do not impart long-term suspension ability.

There is presently a desire in the consumer products industry to provide for transparent surfactant-thickened systems with particulates suspended therein, as well as a suspension aid for high surfactant systems where many alternative thickeners will not function.

It has been discovered that microfibrous cellulose (MFC), bacterially derived or otherwise, can be used to provide suspension of particulates in surfactant-thickened systems as well as in formulations with high surfactant concentrations. It was also discovered that the MFC may be used for this purpose with or without co-agents. When bacterially-derived microfibrous cellulose is utilized, cellular debris can be eliminated which results in transparent solutions at typical use levels.

The microfibrous cellulose appears unaffected by the surfactant micelle development and maintains good suspension in these systems. Microfibrous cellulose is unique in its ability to function in these systems in large part because it is dispersed rather than solubilized, thereby achieving the desired suspension properties in formulations that would otherwise display the hazing and/or precipitation often seen using alternative solubilized polymers.

BRIEF SUMMARY OF THE INVENTION

Surfactant systems comprising microfibrous cellulose are described. "Surfactant systems" is intended to include but is not limited to surfactant-thickened and high surfactant systems. Microfibrous cellulose (MFC) includes MFC prepared by microbial fermentation or MFC prepared by mechanically disrupting/altering cereal, wood, or cotton-based cellulose fibers. When bacterially-derived microfibrous cellulose is utilized, cellular debris can be eliminated which results in transparent solutions at typical use levels. The present invention utilizes surfactants to achieve a very thick (highly viscous) system at high shear rates with particulates suspended therein by using microfibrous cellulose.

The surfactant concentration of these systems ranges from about 5% to about 50% (w/w active surfactant) wherein the specific concentration is product dependent. Body washes typically contain about 5% to about 15% (w/w) surfactant, dishwashing liquids typically contain about 20% to about 40% (w/w) surfactant (with 40% being an "ultra" concentrated product), and laundry detergents typically contain about 15% to about 50% (w/w) surfactant.

The MFC is present at concentrations from about 0.05% to about 1.0%, but the concentration will depend on the desired product. For example, while about 0.06% (w/w) MFC is preferred for suspending small alginate beads in a body wash, about 0.075% is preferred for suspending air bubbles in a body wash, and about 0.150% (w/w) is preferred for suspending either air bubbles or beads in a system containing about 40% (w/w) surfactant. Furthermore, the concentration of MFC will be adjusted accordingly if a highly transparent system is desired. Specifically, a very transparent body wash at about 5% to about 15% (w/w active surfactant) can be achieved with a MFC level of from about 0.055 to about 0.25% (w/w active surfactant).

Particulates to be suspended could include aesthetic agents (decorative beads, pearlescents, air bubbles, fragrance beads, etc.) or active ingredients (insoluble enzymes, encapsulated actives such as moisturizers, zeolites, exfoliating agents (e.g. alpha hydroxyl and/or glycolic acids or polyethylene beads), vitamins (e.g. vitamin E) etc. or both. Other suitable particulates would be apparent to one of skill in the art.

The invention is also directed to the use of co-agents and/or co-processing agents such as CMC, xanthan, and/or guar gum with the microfibrous cellulose in the surfactant systems described herein. Microfibrous cellulose blends are microfibrous cellulose products which contain co-agents. Two blends are described MFC, xanthan gum, and CMC in a ratio of 6:3:1, and MFC, guar gum, and CMC in a ratio of 3:1:1. These blends allow MFC to be prepared as a dry product which can be "activated" with high shear or high extensional mixing into water or other water-based solutions. "Activation" occurs when the MFC blends are added to water and the co-agents/co-processing agents are hydrated. After the hydration of the co-agents/co-processing agents, high shear is generally then needed to effectively disperse the microfibrous cellulose fibers to produce a three-dimensional functional network that exhibits a true yield point. Unexpectedly, the co-agent and/or co-processing agents CMC, xanthan, and/or guar gum present in these microfibrous cellulose blends appear to remain solubilized (after activation in water) in many high surfactant formulations despite their general lack of compatibility in the high surfactant systems, most likely due to the low use level of these polymers in these formulations with MFC.

The invention is further directed to methods of making the surfactant systems described, with or without co-agents and/or co-processing agents.

BRIEF DESCRIPTION OF THE SEVERAL VIEWS OF THE DRAWINGS

FIG. 1 provides an illustration of a microfibrous cellulose blend in a surfactant thickened body wash with bubbles suspended therein.

FIG. 2 provides an illustration of a microfibrous cellulose blend in a surfactant thickened body wash with alginate beads suspended therein.

FIG. 3 provides two illustrations of microfibrous cellulose blends in ultra concentrated dish soaps.

DETAILED DESCRIPTION OF THE INVENTION

Figure 4:
FIG. 4 provides an illustration of a microfibrous cellulose blend in an ultra concentrated liquid laundry detergent.

Body wash formulations demonstrating both the surfactant-thickening and suspension properties using a 0.125% MFC/xanthan/CMC (6:3:1) blend are described in Examples 1 and 2. The body washes exhibit very good clarity and the ability to suspend air bubbles and beads.

Manual dishwashing liquid and liquid laundry detergents, which have a higher surfactant level than found in body washes, are also described. Manual dishwashing liquids with alginate suspended therein are described in Example 3.

A liquid laundry detergent with fragrance beads suspended therein is described in Example 4.

A wet-cake form of microfibrous cellulose was used in Example 5 for preparing a high surfactant system comprising a concentrated liquid laundry soap with air bubbles suspended therein.

Example 1

A liquid body wash with air bubbles was prepared. FIG. 1 displays the clarity and suspensive qualities of this system. The resulting body wash exhibited very thick surfactant rheology based on visual inspection, possessed the ability to suspend air bubbles, and a yield value of about 3.4 Pa (as measured with a Brookfield® Yield Rheometer).

Step A: Deionizied water, 10% NaCl solution, and Kathon® CG were added to a small Oster® mixing jar. Microfibrous cellulose (MFC/xanthan/CMC 6:3:1 blend) was added to the top of the water and then the Oster® mixer blade was assembled and the combination was mixed at top speed for 5 minutes ("Liquify" speed).

Step B: The contents were transferred to a 400 mL tall-form beaker with a paint mixing blade. Sodium laureth sulfate (JEELATE® ES-3) was added to the solution described in Step A and mixed at about 1000 rpm for 5 minutes. Sodium cocamidopropyl betaine (JEETERIC® CAB-LC) was then added to the mix and mixed an additional 5 minutes at 1000 rpm. Fragrance was then added.

Step C: Cocamide DEA was added to the solution described in Step B. Thickening occurred as more DEA was added. Citric Acid was then added as a 50% solution to reduce the pH to the desired level (pH 5.5 in this case). The contents were removed form the mixer. Air entrained during mixing was stabilized by the presence of the MFC/xanthan/CMC 6:3:1 blend.

TABLE 1

Body Wash Shower Gel

| Process Step | Ingredient | % (w/w) | Grams |
|---|---|---|---|
| A | Deionized Water | 54.775 | 219.10 |
|   | Microfibrous Cellulose blend (MFC/xanthan/CMC 6:3:1 blend) | 0.125 | 0.50 |
| A | 10% NaCl Solution | 5.00 | 20.00 |
| A | Kathon CG | 0.10 | 0.40 |
| B | Jeeteric ® CAB-LC sodium cocamidopropyl betain | 7.00 | 28.00 |
| B | Jeelate ® ES-3 Sodium Laureth Sulfate | 25.00 | 100.00 |
| B | Fragrance | 1.00 | 4.00 |
| C | Cocamide DEA | 7.00 | 28.00 |
| C | Citric Acid (50% solution) | To Suit | To Suit |
| Totals | | 100.00 | 400.00 |

Example 2

A body wash was prepared as described in Example 1 but incorporated the suspension of beads instead of air bubbles. Alginate beads were added as the conclusion of step C. A visual representation of this embodiment can be seen in FIG. 2.

Example 3

High surfactant systems were prepared using manual dishwashing liquid and laundry detergent. Alginate beads or air was suspended in the solutions. Palmolive Ultra® dish soap was diluted in half to make a "normal" concentration dish soap. A concentrate was first prepared containing 0.25% microfibrous cellulose blend (MFC/xanthan/CMC 6:3:1 blend) in deionized water. The concentrate was made by mixing the solution on an Oster® blender at "liquefy" (top speed) for 5 minutes. The microfibrous cellulose mixture was then diluted 1:1 with Palmolive Ultra® detergent or Dawn Ultra® detergent (the Palmolive® contained 0.1% triclosan) using a paint mixing or propeller blade. The dish soap was added to the microfibrous cellulose solution while mixing. Excellent clarity and suspension of air and/or alginate beads were achieved for both the Palmolive Ultra® detergent and Dawn Ultra® detergent samples. The microfibrous cellulose diluted well notwithstanding the relative low shear of the paint or propeller mixing blade. The yield point for these solutions was about 2.5 Pa. A visual representation can be found in FIG. 3.

Example 4

A high surfactant system using a concentrated liquid laundry soap was prepared. "All Small and Mighty® three times concentrated" detergent was used. A 0.25% microfibrous cellulose blend (MFC/xanthan/CMC 6:3:1 blend) concentrate was activated in distilled water with an Oster® blender set at top speed (liquefy). Mix time was 5 minutes. The microfibrous cellulose solution was diluted 1:1 with All Small and Mighty® three times concentrated detergent. Very good clarity and suspension was achieved for the dilution resulting in a yield point of 0.62 Pa. The detergents were put in a 45° C. oven to assess heat stability and showed excellent stability with no loss in clarity or suspension over 4 weeks of aging. A visual representation can be seen in FIG. 4.

Example 5

Figure 5:
FIG. 5 provides an illustration of a microfibrous cellulose in an ultra concentrated liquid laundry detergent with air bubbles suspended therein.

A high surfactant system using a concentrated liquid laundry soap was prepared using the wet-cake version of microfibrous cellulose. "All Small and Mighty three times concentrated" detergent was used. A 1.56% wet-cake microfibrous cellulose concentrate was activated in distilled water with an Oster® blender set at top speed (liquefy). Mix time was 5 minutes. The activity (% solids) of this wet-cake form of MFC was about 16% so the active MFC level was about 0.25% in the concentrate. The microfibrous cellulose solution was diluted 1:1 with All Small and Mighty® three times concentrated detergent. Very good suspension was achieved for the dilution resulting in a yield point of 13 Pa. A visual representation can be seen in FIG. 5.

The invention claimed is:

1. An aqueous composition comprising a surfactant-thickened system consisting essentially of water, a bacterial-derived microfibrous cellulose present in the aqueous composition at a concentration from about 0.05% to about 0.15% (w/w), a surfactant present in the aqueous composition at a concentration from 5% to about 20% (w/w active surfactant), a salt, a suspended particulate, and a co-agent, wherein the aqueous composition is clear.

2. The composition according to claim 1, wherein the microfibrous cellulose is present in the aqueous composition at a concentration about 0.06%.

3. The composition according to claim 2, wherein the surfactant is present in the aqueous composition at a concentration from 5% to about 15% (w/w active surfactant).

4. The composition according to claim 3, wherein the suspended particulate is selected from the group consisting of air bubbles, beads, and a combination thereof.

5. The composition according to claim 1, wherein the microfibrous cellulose is present in the aqueous composition at a concentration of about 0.075%.

6. The composition according to claim 1, wherein the microfibrous cellulose is present in the aqueous composition at a concentration of about 0.09%.

7. The aqueous composition according to claim 1, wherein the composition is a body wash, a shampoo, a dishwashing detergent, a laundry detergent, or an automotive detergent.

8. The aqueous composition of claim 1, wherein the surfactant is selected from the group consisting of sodium laureth sulfate, sodium cocamidopropyl betain, and combinations thereof.

9. The aqueous composition of claim 1, wherein the salt is sodium chloride.

10. An aqueous composition comprising a high surfactant system consisting essentially of water, a bacterial-derived microfibrous cellulose, a surfactant, a suspended particulate, and optionally a co-agent, prepared by a method comprising the steps of:

combining a powdered microfibrous cellulose with water and mixing with high shear,
adding a surfactant and then mixing, and
adding particulates followed by mixing,
wherein the microfibrous cellulose is present in the aqueous composition at a concentration from about 0.05% to about 0.15% (w/w), the surfactant is present in the aqueous composition at a concentration from about 20% to about 50% (w/w active surfactant), and wherein the resulting composition is clear and the particulates are suspended therein.

11. The aqueous composition of claim 10 wherein the microfibrous cellulose is present in the aqueous composition at a concentration of about 0.06%.

12. The aqueous composition of claim 10, wherein the microfibrous cellulose is present in the aqueous composition at a concentration of about 0.075%.

13. The aqueous composition of claim 10, wherein the microfibrous cellulose is present in the aqueous composition at a concentration of about 0.09%.

14. The aqueous composition of claim 10, wherein the surfactant is present in the aqueous composition at a concentration from about 20% to about 40% (w/w active surfactant).

15. The aqueous composition of claim 10, wherein the particulates are selected from the group consisting of air bubbles, beads, and a combination thereof.

16. A surfactant system consisting essentially of water, a microfibrous cellulose blend, a surfactant, and a suspended particulate, wherein the microfibrous cellulose blend is a blend of a bacterial-derived microfibrous cellulose, xanthan gum, and carboxymethyl-cellulose in a ratio of 6:3:1.

17. An aqueous composition comprising the surfactant system of claim 16, wherein the microfibrous cellulose blend is present in the aqueous composition at a concentration of about 0.125% (w/w).

18. A surfactant system consisting essentially of water, a microfibrous cellulose blend, a surfactant, and a suspended particulate, wherein the microfibrous cellulose blend is a blend of a bacterial-derived microfibrous cellulose, guar gum, and carboxymethylcellulose in a ratio of 3:1:1.

19. An aqueous composition comprising a high surfactant system consisting essentially of water, a bacterial-derived microfibrous cellulose present in the aqueous composition at a concentration from about 0.05% to about 0.15% (w/w), a surfactant present in the aqueous composition at a concentration from about 20% to about 50% (w/w active surfactant), a suspended particulate, and optionally a co-agent, wherein the aqueous composition is clear.

20. The aqueous composition of claim 19, wherein the microfibrous cellulose is present in the aqueous composition at a concentration from about 0.06% to about 0.09% (w/w).

21. The aqueous composition of claim 19, wherein the surfactant is present in the aqueous composition at a concentration from about 20% to about 40% (w/w active surfactant).

22. The aqueous composition of claim 19, wherein the microfibrous cellulose and co-agent is a blend of microfibrous cellulose, guar gum, and carboxymethylcellulose in a ratio of 3:1:1.

23. The aqueous composition of claim 19, wherein the microfibrous cellulose and co-agent is a blend of microfibrous cellulose, xanthan gum, and carboxymethyl-cellulose in a ratio of 6:3:1.

24. The aqueous composition of claim 19, wherein the composition is a body wash, a shampoo, a dishwashing detergent, a laundry detergent, or an automotive detergent.

* * * * *